US00PP21568P2

(12) United States Plant Patent
Morgan

(10) Patent No.: US PP21,568 P2
(45) Date of Patent: Dec. 14, 2010

(54) CITRUS TREE NAMED 'MORGAN SUNRISE NAVEL'

(50) Latin Name: *Citrus sinensis*
Varietal Denomination: Morgan Sunrise Navel

(76) Inventor: Billy Mac Morgan, 26349 Road 192, Exeter, CA (US) 93221

( * ) Notice: Subject to any disclaimer, the term of this patent is extended or adjusted under 35 U.S.C. 154(b) by 0 days.

(21) Appl. No.: 12/454,596

(22) Filed: May 20, 2009

(51) Int. Cl.
*A01H 5/00* (2006.01)

(52) U.S. Cl. ..... Plt./202
(58) Field of Classification Search ..... Plt./202
See application file for complete search history.

*Primary Examiner*—Susan B McCormick Ewoldt
(74) *Attorney, Agent, or Firm*—Knobbe, Martens, Olson & Bear, LLP

(57) ABSTRACT

A new and distinct variety of citrus tree (*Citrus sinensis* (L.) Osbeck), which has the variety denomination 'Morgan Sunrise Navel', and which produces a sweet fruit which is mature for harvesting and shipment approximately February 10 to April 15, under the ecological conditions prevailing in the San Joaquin Valley of central California.

6 Drawing Sheets

Latin name of the genus and species claimed: *Citrus sinensis.*

Variety denomination: 'MORGAN SUNRISE NAVEL'.

BACKGROUND OF THE INVENTION

The present invention relates to a new and distinct variety of orange tree, *Citrus sinensis* (L.) Osbeck, which has been given the variety name 'Morgan Sunrise Navel'.

Origin

The Morgan Sunrise Navel variety of orange tree was discovered in 1999 by the inventor in his cultivated, commercial grove of two year old 'Cara Cara' (unpatented) navel orange trees. The current variety and subject of this application was believed to be a whole tree of 'Cara Cara' (unpatented) navel orange tree when planted. The present variety was discovered as a whole plant mutation (sport).

Asexual Reproduction

Asexual reproduction of this new and distinct variety of 'Morgan Sunrise Navel' was accomplished by budding the new citrus tree onto 'Carrizzo' rootstock (unpatented). This asexual reproduction was performed in the San Joaquin Valley of California in the spring of 2004. Subsequent evaluations of this asexually reproduced variety have shown that the asexual reproductions run true to the original tree. All characteristics of the original tree and its fruit were established and appear to be transmitted through these succeeding asexual propagations.

SUMMARY OF THE INVENTION

The 'Morgan Sunrise Navel' is an orange citrus tree and is characterized by producing fruit which is firmer and which hangs on the tree longer and later than the 'Cara Cara' (unpatented) navel citrus variety, which is the closest similar commercial variety. In comparison to the 'Cara Cara' (unpatented) navel citrus variety, the 'Morgan Sunrise Navel' bears more fruit (generally 10-15) throughout the length of a fruiting lateral (one year old growth), whereas fewer fruit (generally 2-3 clusters or 4-7 fruit) were born on the 'Cara Cara'

(unpatented) citrus variety on comparatively similar fruiting wood. In addition to the foregoing, the fruit of the new tree also appears to have good handling and shipping qualities.

BRIEF DESCRIPTION OF THE DRAWINGS

The accompanying drawings are color photographs of the new citrus tree variety. The colors in this photograph are as nearly true as is reasonably possible in a color representation of this type. Due to chemical development, processing, and printing, the leaves and fruit depicted in these photographs may or may not be accurate when compared to the actual specimen. For this reason, future color references should be made to the color plates (Royal Horticultural Society) and descriptions provided hereinafter.

DETAILED DESCRIPTION OF THE PREFERRED EMBODIMENT

Figure 1:
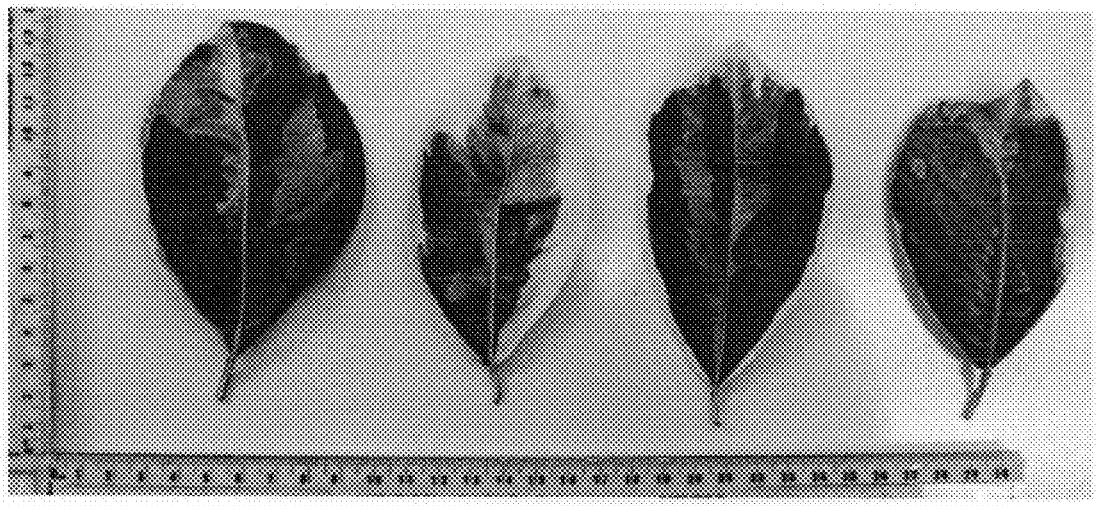
FIG. 1 displays vegetative shoots of the typical leaves of the 'Morgan Sunrise Navel'. They are representative of the variation of colors, size, and texture of the leaves.
Figure 2:
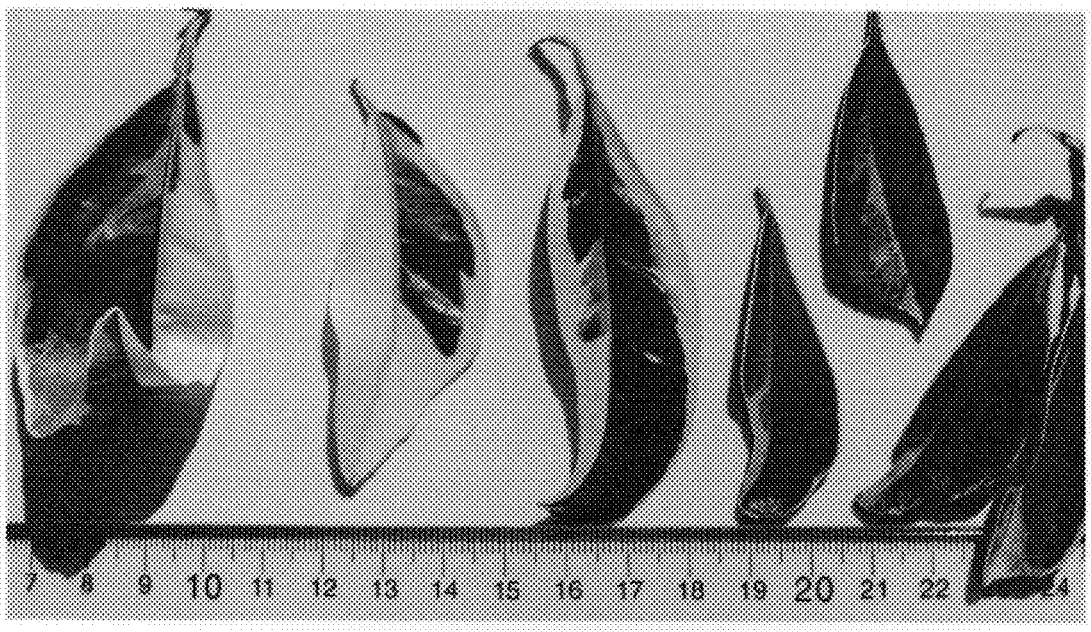
FIG. 2 also displays vegetative shoots of the typical leaves of the 'Morgan Sunrise Navel'. They are also representative of the variation of colors, size, and texture of the leaves.
Figure 3:
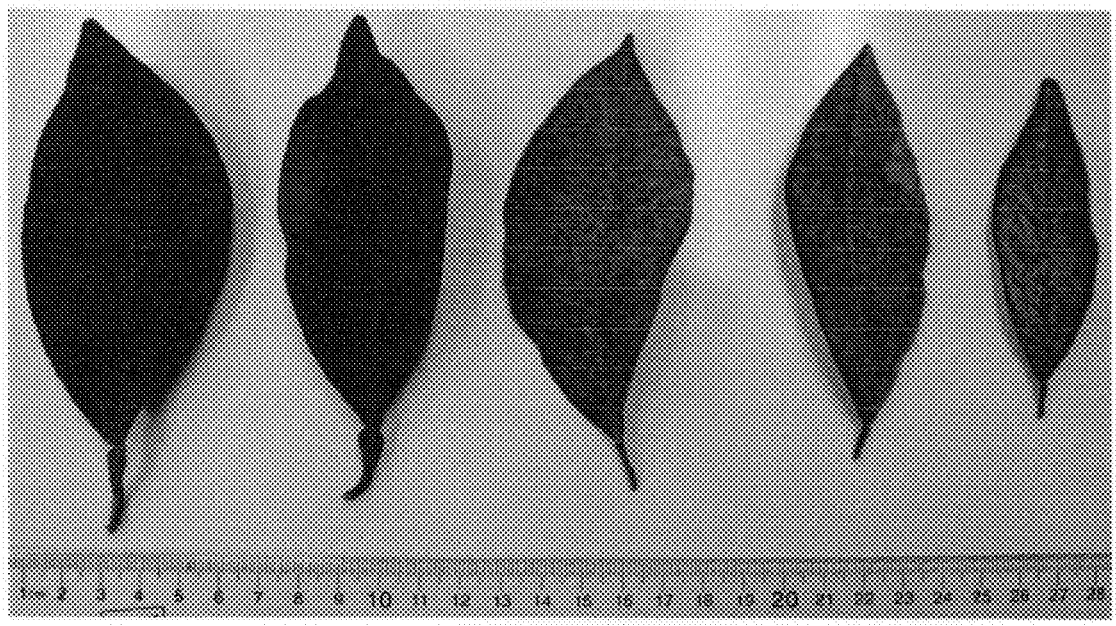
FIG. 3 is a comparative to the 'Cara Cara' (unpatented) navel tree leaves. It compares the leaf shape and coloring.
Figure 4:
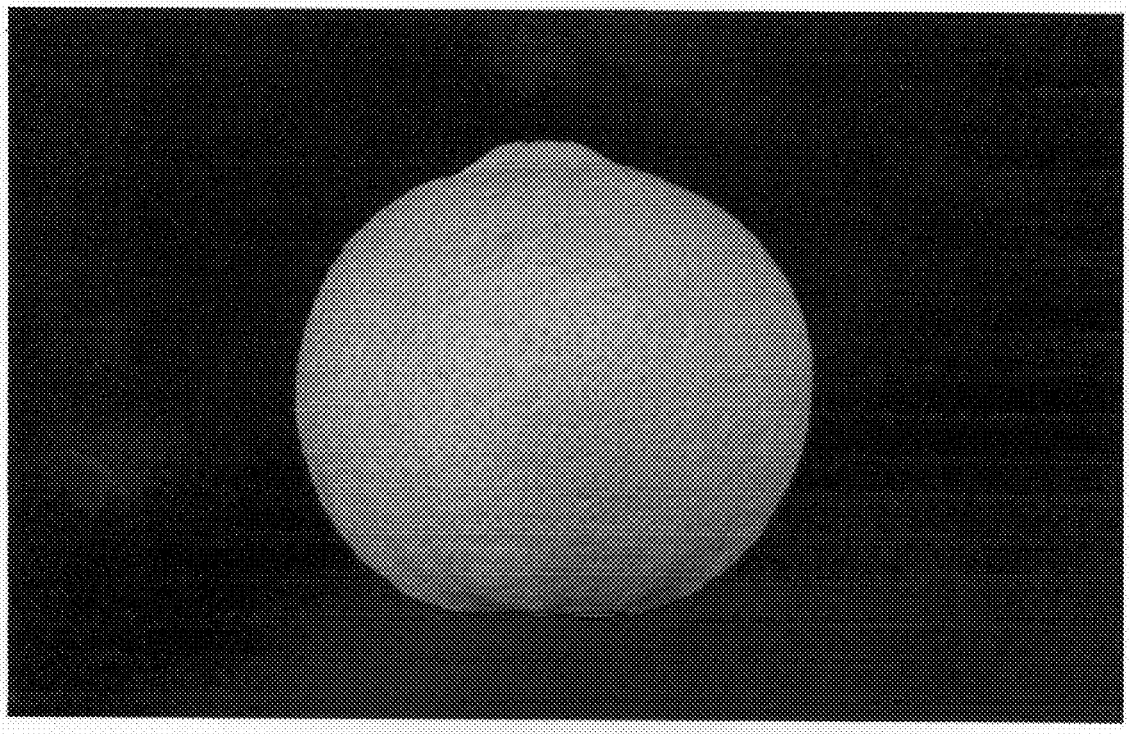
FIG. 4 is a lateral view of the fruit of the variety 'Morgan Sunrise Navel'.
Figure 5:
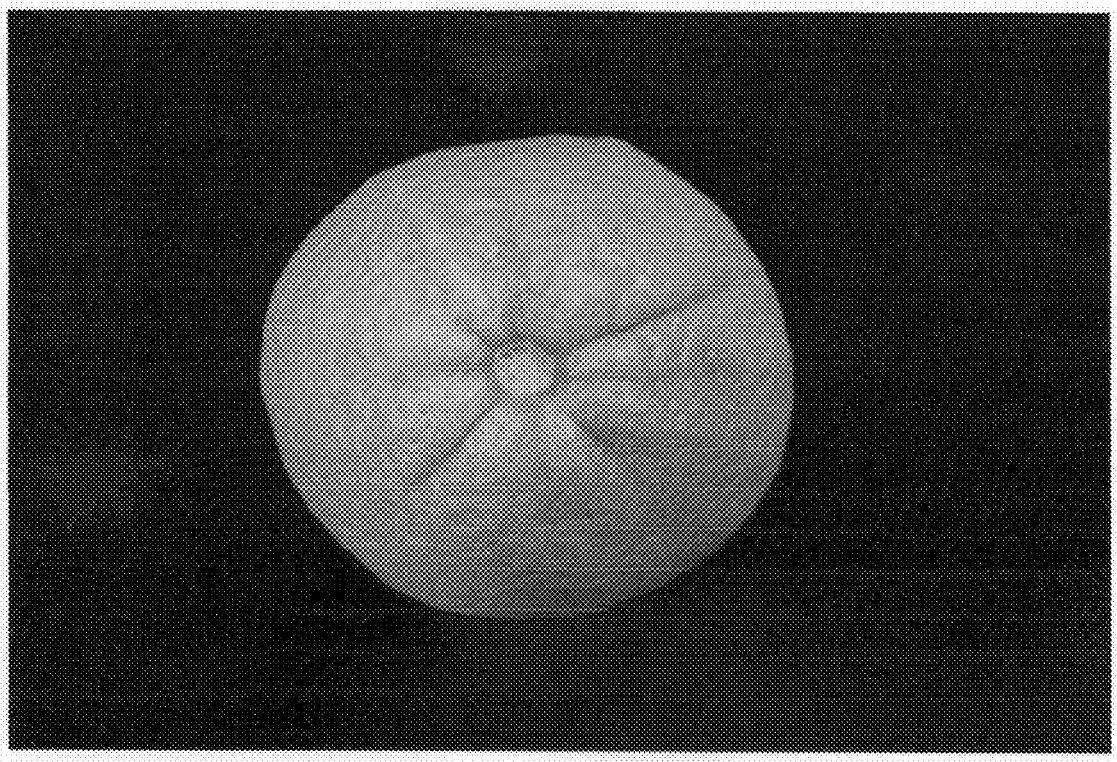
FIG. 5 is a basal view of the fruit of the variety 'Morgan Sunrise Navel'.
Figure 6:
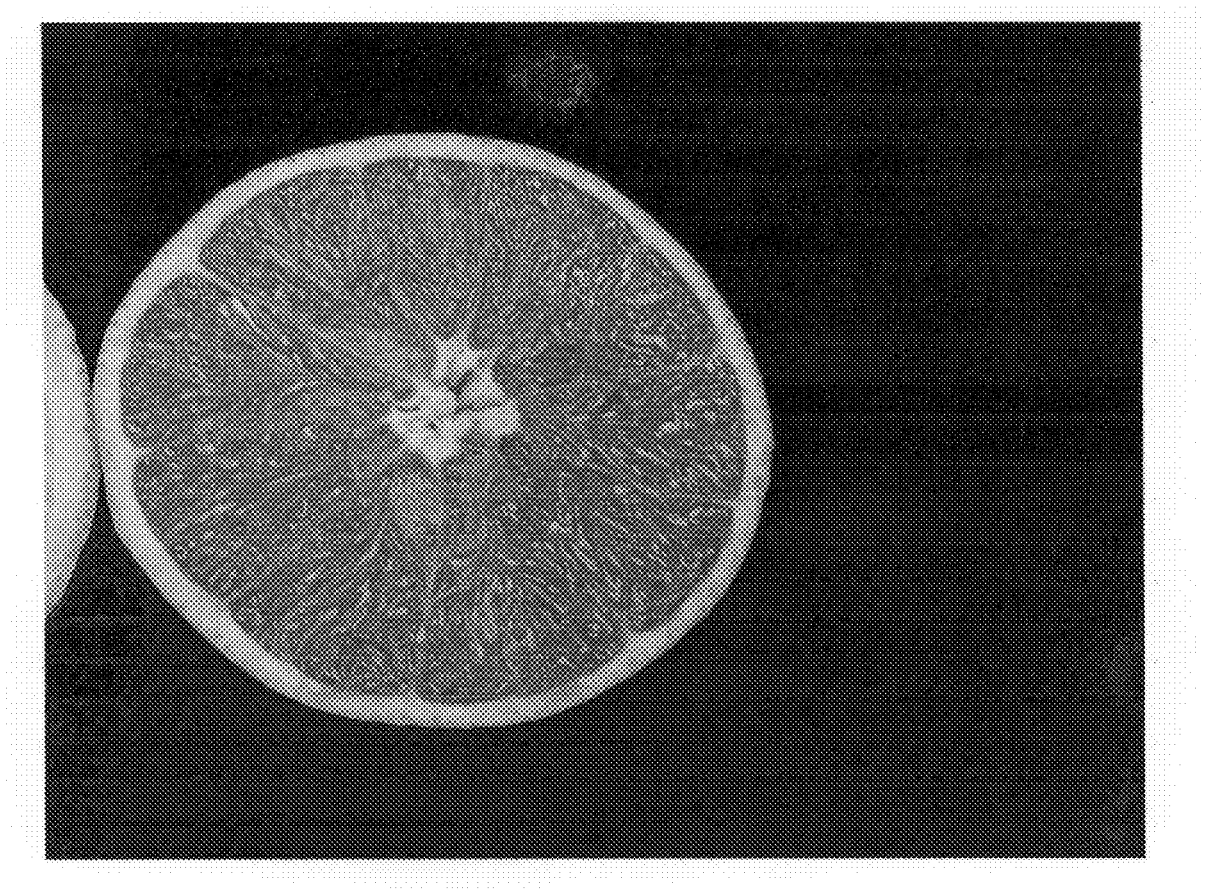
FIG. 6 is an equatorial cross section exposing flesh of the fruit of the variety 'Morgan Sunrise Navel'.

Referring more specifically to the pomological details of this new and distinct variety of citrus tree, the following has been observed during the tenth fruiting season on the original tree and the third fruiting season on subsequent propagations. All major color code designations are by reference to The R.H.S. Colour Chart (Fourth Edition) provided by The Royal Horticultural Society of Great Britain. Common color names are also occasionally used.

Tree:

*Size.*—Generally — Considered medium when compared to other common commercial naval orange cultivars.

*Vigor.*—The overall vigor of the present of variety is considered slightly less vigorous than what is characteristic for the 'Cara Cara' (unpatented) naval citrus variety. Considered of moderate vigor. The present naval orange tree variety grew to about 3.80 meters in its 10th year of growth.

*Productivity.*—Productive. Fruit set varies from about 2.0 to several times more crop than the crop load set by the 'Cara Cara' (unpatented) navel citrus tree. The number of the fruit set varies with the prevailing climatic conditions and cultural practices employed during the bloom period. The current variety is more precocious than the 'Cara Cara' (unpatented) variety (bearing heavier crops in the earlier years).

*Bearer.*—Regular. Fruit set has been heavy during the previous years of observation.

*Form.*—Somewhat upright. Generally more upright than that of the 'Cara Cara' (unpatented) naval citrus tree.

*Density.*—Open, airy. Not a dense canopy.

*Hardiness.*—The present tree was grown and evaluated in USDA Hardiness Zone 9.

Trunk:

*Diameter.*—Approximately 33.0 cm in diameter when measured at a distance of approximately 10.0 cm above the soil level. This measurement was taken at the end of the tenth growing season.

*Bark texture.*—Smooth.

*Lenticels.*—Approximately 10 per cm squared.

*Bark coloration.*—Approximately RHS Grey-Brown N199A plus N199B, with 199B.

*Thorns.*—Thorns are present on mature and juvenile wood. Thorns generally range from approximately 1.0 mm to approximately 12.0 mm and are smaller on less mature wood and larger on more mature wood. Their color is Light yellow green and ranges from approximately RHS 2D to approximately RHS 145A.

Branches:

*Size.*—Considered medium for the variety.

*Diameter.*—15.5 cm (measured at 1.02 meters high); 9 cm (measured at 1.83 meters high).

*Surface texture.*—Consider somewhat smooth, unfurrowed. Same texture as trunk.

*Current season shoots.*—Surface texture — Substantially glabrous.

*Internode length.*—Approximately 2.0 cm.

*Color of mature branches.*—Approximately RHS N199A plus N199B.

*Current seasons shoots.*—Color — Generally Yellow Green Group, RHS 144B, with some 144A.

Leaves — which exhibits a variegated leaf coloration pattern:

*Size.*—Considered medium small for the species. Leaf measurements have been taken from vigorous, upright, current-season growth at approximately mid-shoot.

*Length.*—Approximately 55.0 to about 100.0 millimeters.

*Width.*—Approximately 20.0 to about 72.0 millimeters.

*Base shape.*—Generally rounded, rarely acute.

*Form.*—Oval. Occasionally exhibiting a sinus margin (indent) beginning near the apical tip.

*Tip form.*—Considered slightly mucro but not sharply mucronate.

*Color (color of variegation).*—Upper Leaf Surface — Considered Dark green, Approximately RHS Green Group 137B, plus Yellow Green Group 148B, plus Yellow Group 11C.

*Texture.*—Glabrous.

*Color.*—Lower Leaf Surface — Approximately Medium green, RHS Yellow Green Group 147B, plus Yellow Green Group 148B, plus Yellow Green Group 148C, plus Yellow Group 11C.

*Venation.*—Pinnately veined.

*Mid-vein.*—Color — Considered a light yellow-green, RHS Yellow-Green Group 144A, in the early to mid period of the growing season.

*Margins.*—Slightly to strongly undulating.

*Form.*—Very finely crenate. Considered smooth.

*Uniformity.*—Considered generally uniform. Some lateral margins of leaves can exhibit a 'boating' effect where the sides rise upward creating what resembles boat shaped gunnels (walls).

*Petiole size.*—Considered medium long.

*Petiole length.*—Approximately 8.0 to about 10.0 mm.

*Petiole diameter.*—Approximately 1.0 to about 2.0 mm.

*Petiole color.*—Considered Pale green, RHS Yellow Green Group 144A.

*Stipules.*—Often present. Stipules, when present are completely attached to the stem along the length of their structure (from their basal appearance (often 5-8.0 mm above the basal end) to the beginning of the leaf margin), are smooth margined, and resemble a small thin laterally positioned 'leaf fin'. Most often the stipules when noted are in pairs with one on each lateral side of the petiole.

*Stipule size.*—Small.

*Stipule number.*—Often two. Usually one per side.

*Stipule form.*—Extremely oblong, blunted.

*Stipule color.*—Majority of Stipules considered, Yellow Green Group RHS 148C, with Yellow Group 11B. This characteristic is dependent upon leaf color variation at base of leaf.

Flowers:

*Flower buds.*—Generally — Depending upon the stage of development, the flower buds are approximately 8.0 millimeters wide; about 11.0 millimeters long; conic in form; and slightly appressed relative to the bearing shoot.

*Flower buds.*—Color — This characteristic is dependent upon the proximity to the bloom. For example, flower buds approximately 7-10 days to bloom are about RHS 153C, while flower buds approximately 14 days to bloom are about RHS 150B.

*Hardiness.*—The current variety has not been intentionally subjected to drought, freezing temperatures or heat stress, and therefore this information is not available.

*Date of first bloom.*—Observed approximately March 16.

*Blooming time.*—Generally typical for citrus varieties in the San Joaquin Valley.

*Duration of bloom.*—Approximately 50 days. This characteristic varies slightly with the prevailing climatic conditions.

*Flower type.*—Perfect.

*Flower size.*—The flower diameter at full bloom is approximately 20.0 to about 23.0 millimeters.

*Bloom quantity.*—Considered very abundant.

*Petal size.*—Generally — Considered medium for the species.

*Petal length.*—Approximately 8.0 to about 11.0 millimeters.

*Petal width.*—Approximately 3.0 to about 6.0 millimeters.

*Petal form.*—Considered oblong.

*Petal count.*—Nearly always 5, Occasionally 4 and 6 petals can be observed.

*Petal texture.*—Slightly glabrous but fleshy (slightly rubbery).

*Petal color.*—White, considered RHS White Group 155C.

*Fragrance.*—Mild, abundant.

*Petal margins.*—Generally — Smooth.

*Petal apex.*—Rounded.

*Pedicel length.*—Approximately 10.0 mm.

*Pedicel diameter.*—Approximately 2.0 mm.

*Pedicel color.*—Considered Yellow Green Group — RHS 144A.

*Sepals.*—Average of 5, some occurrence of 4.

*Surface texture.*—Generally glabrous.

*Sepal size.*—3.0 mm.

*Sepal color.*—Considered Yellow Green Group — RHS 144A, with RHS 145A.

*Anther count.*—Approximately 25. Some occurrence of 23 to 28.

*Anther color.*—Considered White Group RHS 155D.

*Pollen production.*—Pollen is abundant, and is approximately RHS Greyed-Orange Group 163B.

*Fertility.*—Current variety produces pollen.

*Filament size.*—Length is variable, approximately 6.0 mm to about 8.0 millimeters long.

*Filament color.*—Considered white, RHS 155C.

*Pistil number.*—Usually 1.

*Pistils.*—Generally — Average in size.

*Pistil length.*—Approximately 7.0 to about 9.0 millimeters including the ovary.

*Pistil color.*—Considered RHS White Group 155A.

*Pistil surface texture.*—The variety has a long pubescent pistil.

Fruit:

*Maturity when described.*—Firm ripe condition (shipping ripe).

*Date of first picking.*—Approximately February 10.

*Date of last picking.*—Typically April 15. The date of harvest varies slightly with the prevailing climatic conditions.

*Size.*—Generally — Considered average to good size.

*Average latitudinal diameter.*—Approximately 75 mm to about 90.0 millimeters.

*Average longitudinal diameter.*—Approximately 78.0 mm to about 92.0 millimeters.

*Typical weight.*—Approximately 226.80 grams to approximately 425.24 grams. This characteristic is highly dependent upon the prevailing cultural practices and climatic conditions, and therefore is not particularly distinctive of the variety.

*Fruit form.*—Generally — Considered rounded to slightly elongate in the vertical axis. The fruit is generally uniform in symmetry.

*Apex.*—Rounded with a navel protrusion. Navel is pronounced but considered tight with internal folds not visible.

*Base.*—Even and rounded.

*Rind.*—Considered glabrous.

*Texture.*—Surface is uniformly pitted with oil glands.

*Color.*—(May 2009) — Considered RHS Orange Group N25C, plus Orange Group 26A. Thickness — Considered medium in thickness. Approximately 4.0 mm thick. Even though the rind surface exhibits lighter strands of coloration (variegation) during fruit development than that of the general surface color, at maturity the presence of rind color variation is almost completely absent.

*Flesh ripening.*—Considered even.

*Flesh texture.*—Firm, juicy, and dense.

*Aroma.*—Very slight.

*Fruit use.*—Fresh market.

*Eating quality.*—Considered very good.

*Flavor.*—Considered sweet and mildly acidic. The flavor is considered both pleasant and balanced.

*Juice production.*—Moderate.

*Brix.*—About 13.0 degrees. This characteristic varies slightly with the number of fruit per tree; prevailing cultural practices; and the surrounding climatic conditions.

*Flesh color.*—Pale yellow-orange, (approximately RHS Yellow-Orange Group 20D).

*Keeping quality.*—Appears excellent.

*Shipping quality.*—Good. Considered commercial.

*Resistance to insects and disease.*—No particular susceptibilities were noted. The present variety has not been tested to expose or detect any susceptibilities or resistances to any known plant and/or fruit diseases.

Although the new variety of citrus navel tree possesses the described characteristics when grown under the ecological conditions prevailing near Exeter, Calif., in the San Joaquin Valley of California, it should be understood that variations of the usual magnitude and characteristics incident to changes in growing conditions, fertilization, pruning, pest control and horticultural management are to be expected.

What is claimed is:

1. A new distinct variety of citrus tree, 'Morgan Sunrise Navel', substantially as herein illustrated and described.

* * * * *